(12) United States Patent
Hoskuldsson

(10) Patent No.: US 8,924,226 B2
(45) Date of Patent: Dec. 30, 2014

(54) INTERACTIVE TESTING SYSTEM FOR ANALYSING BIOLOGICAL SAMPLES

(75) Inventor: Agnar Hoskuldsson, Kgs. Lyngby (DK)

(73) Assignee: Sime Diagnostics ApS, Lyngby (DK)

( * ) Notice: Subject to any disclaimer, the term of this patent is extended or adjusted under 35 U.S.C. 154(b) by 1138 days.

(21) Appl. No.: 12/377,611

(22) PCT Filed: Aug. 15, 2007

(86) PCT No.: PCT/DK2007/050106
§ 371 (c)(1),
(2), (4) Date: Jun. 4, 2009

(87) PCT Pub. No.: WO2008/019695
PCT Pub. Date: Feb. 21, 2008

(65) Prior Publication Data
US 2010/0241442 A1    Sep. 23, 2010

Related U.S. Application Data

(60) Provisional application No. 60/822,549, filed on Aug. 16, 2006.

(30) Foreign Application Priority Data

Aug. 16, 2006   (DK) ................................. 2006 01067

(51) Int. Cl.
*G06F 19/00*   (2011.01)
*G06F 17/30*   (2006.01)
*G06Q 50/22*   (2012.01)

(52) U.S. Cl.
USPC .................................................. 705/2; 705/3

(58) Field of Classification Search
USPC .............................................................. 705/2
See application file for complete search history.

(56) References Cited

U.S. PATENT DOCUMENTS

| | | | |
|---|---|---|---|
| 6,024,699 A | 2/2000 | Surwit et al. |
| 6,190,313 B1 | 2/2001 | Hinkle |
| 6,192,320 B1 | 2/2001 | Margrey et al. |
| 6,278,999 B1 | 8/2001 | Knapp |
| 6,602,469 B1 | 8/2003 | Maus et al. |
| 6,844,149 B2 | 1/2005 | Goldman |
| 6,849,045 B2 | 2/2005 | Iliff |
| 6,850,252 B1 | 2/2005 | Hoffberg |
| 6,873,914 B2 | 3/2005 | Winfield et al. |

(Continued)

FOREIGN PATENT DOCUMENTS

EP    1 582 598    10/2005

*Primary Examiner* — Hiep V Nguyen
(74) *Attorney, Agent, or Firm* — Gifford, Krass, Sprinkle, Anderson & Citkowski, P.C.

(57) ABSTRACT

The invention relates to a system and a method for health monitoring service based on a central server. Measurements of biological samples (e.g. blood, saliva and urine) are carried out by a remote measurement system. The measurement data are sent to a central server, where the data are processed and analyzed, for example by expert knowledge systems, and a health profile generated is sent back to the remote measurement system. A health care provider may receive the results of the analysis carried out by the expert knowledge system, and the health care provider may further upload laboratory measurements, which can be included in the health analysis of the person. It is preferred that the system and method according to the invention is capable of providing an early warning of diseases that causes changes in chemical components in the biological sample.

8 Claims, 7 Drawing Sheets

(56) References Cited

U.S. PATENT DOCUMENTS

| | | |
|---|---|---|
| 6,937,323 B2 | 8/2005 | Worthington et al. |
| 6,963,907 B1 | 11/2005 | McBride et al. |
| 6,966,880 B2 | 11/2005 | Boecker et al. |
| 2002/0049384 A1* | 4/2002 | Davidson et al. ............. 600/454 |
| 2007/0239367 A1* | 10/2007 | Odegard et al. ................ 702/30 |

* cited by examiner

INTERACTIVE TESTING SYSTEM FOR ANALYSING BIOLOGICAL SAMPLES

The present invention relates to a system and a method for health monitoring service based on a central server. Measurements of biological samples (e.g. blood, saliva and urine) are carried out by a remote measurement system. The measurement data are sent to a central server, where the data are processed and analyzed, for example by expert knowledge systems, and a health profile generated is sent back to the remote measurement system. A health care provider may receive the results of the analysis carried out by the expert knowledge system. The health care provider may upload laboratory measurements, which can be included in the health analysis of the person. It is preferred that the system and method according to the invention is capable of providing an early warning of diseases that causes changes in chemical components in the biological sample.

All patent and non-patent references cited in the application, or in the present application, are also hereby incorporated by reference in their entirety.

BACKGROUND OF INVENTION

Most countries in the world are experiencing great difficulties concerning the hospital expenses. More and more types of illnesses can be treated. Sickness that was impossible to treat last year may be possible to treat now due to more advanced equipments. The pressure on hospitals is creating huge economic and political problems in many countries. The best way to reduce the pressure on hospitals is to reduce the number people that need hospital treatments. New technologies provide with new opportunities in assisting family doctors, medical laboratories and health centres in providing with the health care. The key issue is prevention.

The use of the Internet has provided means for forwarding measurement results from remote locations to central hospitals and other health care providers, i.e. telemedicine or medical telecommunication. Prior art shows several systems where one or another parameter may be measured remotely and the result being forwarded to a central for storage and optionally for forwarding to other interested parties.

U.S. Pat. No. 6,190,313 (Hinkle) discloses for example a system for remotely monitoring the health of a patient to inform the patient as to his/her state of heath by peak expiratory flow measurements. The data obtained from the patient is analysed at the patient's site, and the patient is notified when an indication for a significant change in health status is found and may instruct the patient to contact the health care provider. Online communication between the remote system and a system at the health care provider is described, as well as a central database for storing information. The health care provider may receive information directly from the remote system or via the central database.

U.S. Pat. No. 6,278,999 (Knapp) discloses a system for personal local health digitizers, for example for determination of ovulation time, and a centralised database that collects and stores monitoring data from a large number of individuals. The information obtained locally may be partly processed locally to provide the user with initial information. Physicians connected to the system are allowed to receive information from the centralised database if authorised by the user.

U.S. Pat. No. 6,937,323 (Worthington et al.) discloses a system for chemical and biological testing using a specially designed bio-disc and optical reader attached to a computer. The system may be located at a health center or at the user's private house. Test data are processed remotely and the processed data are forwarded to a central data processing unit connected to the computer through a network for analysis, wherein the analysis include trending and multivariate analysis.

U.S. Pat. No. 6,192,320 (Margrey et al.) discloses an interactive multi-station medical specimen analysis for analysing medical specimens at remote locations and forwarding through a network for evaluating the results of each of the analyses to a central laboratory. Immediate analyses are provided at the remote station to inform the user of the measurement results, whereas trend analyses may be conducted centrally.

U.S. Pat. No. 6,844,149 (Goldman) discloses a system for remotely sample treatment, wherein the sample is arranged on a multi-component strip and chemical components of the blood are detected. The measurement data may be processed locally or at a central unit via a network, such as the internet. Results are be forwarded to a health care provider.

U.S. Pat. No. 6,963,907 (McBride et al.) discloses a system for remotely monitoring a physical parameter, e.g. cardiac function, by positioning a sensor on the individual to be tested. Test measurement data are forwarded via the Internet to a central server having a database for each individual for processing and analysis, including trend analysis, of the data. The database is used to generate a medical life history and trend reporting for each individual. The results of the analyses may be downloaded to the individual and/or the selected physician.

There is a basic need for a service, which can inform of the basic health parameters and provide with an early warning within different types of diseases. Hospitals all over the world are having troubles due to increased number of patients and improved techniques to cure people. If hospitals could receive early warnings concerning these diseases, not only considerable reduction in treatment time is possible, but also much improved chances of recovery for the patients.

SUMMARY OF INVENTION

The present invention relates to a central server based interactive testing system, which receives remote measurements of a biological sample, and carries out health analysis of the person in question. The remote measurement system receives a health profile showing the values of principal components of the biological sample and how they are located relatively to a normal population. The results of the health analysis may be communicated to the health care provider in medical terms. The health care provider may upload further measurements, which can be included in the analysis.

Thus, the aim of the present invention is to provide intelligent environments for health promotion and prevention or diseases and disorders. This is obtained by establishing advanced communication and data based service within the health community. Accordingly, in one aspect the invention relates to an interactive testing system for analysing biological samples, said system comprising one or more remote measurement system(s) for measuring a biological sample, said remote measurement system generating measurement data from the measurement of said biological sample, a central server for processing said measurement data thereby generating measurement values and/or measurement profiles, means for allowing said remote measurement instrument to communicate with the central server over a network, in said remote measurement system means for forwarding measurement data from the remote measurement system to the central server through the network, and a display unit, in said central server means for generating a health profile from said measurement values, means for storing said measurement values, and means for warding said measurement values and said health profile from said central server to the display unit in the remote system.

In another aspect the invention relates to an interactive testing method for analysing biological samples, said method comprising establishing one or more remote measurement system(s) for measuring a biological sample, said remote measurement system generating measurement data from the measurement of said biological sample, performing a measurement using said remote measurement system obtaining measurement data, forwarding the measurement data to a central server for processing said measurement data thereby generating measurement values and/or profiles, generating, in said central server, a health profile from said measurement values, means for storing said measurement values, and forwarding said health profile from said central server to the remote system, and displaying the health profile.

In one embodiment the interactive testing system comprises decision support for the health care provider by determination of the chemical components of a biological sample, from said remote measurement system, and means for forwarding the values to the said health care provider, a central server for statistical analysis of the chemical components and thereby generating health report, means for allowing said health report to forward to the said health care provider over a network, means for said health care provider to upload laboratory data and means for including those into the general health analysis, in said central server means for generating a health analysis reports from said chemical components and possibly laboratory data, means for storing said reports, and means for forwarding said reports to said health care provider.

The central server will typically contain a very large database that covers numerous types of normal situations and of diseases and disorders. A new sample from an instrument is in general compared in two ways. The first one is comparison to standard population in the database. The result is a health profile of the person compared to the normal population we want to compare with (e.g., age, weight or other measures). It reflects the required analysis. The report may furthermore show the development of the health profile in time. The second one is a check of numerous different situations. There can be checked for numerous different situations, which can be of importance for the person and depending on the type of measurements provided. Standard analysis will typically be to check for indicators of diabetes 2, cancer, cardiovascular diseases and different situations of health risks that can be localised in these liquids (stress, infection, sugar level, fat values etc). The health analysis may preferably be returned within seconds to the person. The results of the analysis are, if this is chosen, forwarded to the doctor. It is important to emphasize that the aim of the service is not necessarily to provide diagnosis of diseases to the remote user. The purpose of the service is to analyse the biological samples and inform the person and possible the doctor if it has been possible to detect some special features of importance for the health.

The main issues for the present invention are

Health profile compared normal population that allow citizens to be informed of their health such that they can improve their life-style and prevent illnesses.

Screening procedures that go through numerous possible situations for detecting important changes or trend both in relation to time and to normal populations.

Tools for doctors/nurses at hospitals/health centres for innovative improvements and learning across fields of medicine.

Intelligent environments for patients such that they can co-operate with their doctor/nurse without being confined to institutional treatment.

Advanced interactive environments for doctors and nurses through connection with the interactive testing system centre which contains a large database on best medical practices.

Best practice and demonstration actions in regional health care networks to extend the database on health care.

A personalised health care service that meets the individual need of people.

DESCRIPTION OF DRAWINGS

FIG. 3 shows a schematic development of diseases, which are checked for.

DETAILED DESCRIPTION OF THE INVENTION

The present invention relate to a system and a method for analysis of health of people. It is an object of the invention to provide a system and a method for servicing users or clients with indications of whether their health is within normal ranges or whether it is recommended to see a health care provider for further examination and analysis. This is provided by a system and a method wherein certain predefined measurement values, such as haemoglobin, blood sugar and cholesterol are extracted from the raw measurement data and compared to references, and addition thereto fingerprints or patterns of the chemical compounds in the biological sample are compared to fingerprints or patterns of chemical compounds found in individuals suffering from specific diseases. Thus, as opposed to the result for a single component, such as blood sugar, a profile will normally relate to the pattern of more than one single component, such as a pattern of several components and their relation to each other, for example as seen as spectra. In order to generate a measurement profile it may not be necessary to extract information of each component, it is simply enough to compare the spectra with references, in that it is not the single component that is analysed but the total pattern or fingerprint of the components. Thereby it is possible to issue an early warning of a coming disease if changes in the chemical components point to the onset of a disease. Therefore, the system and method according to the invention performs measurements of several chemical components in order to provide the necessary chemical profile.

Figure 1:
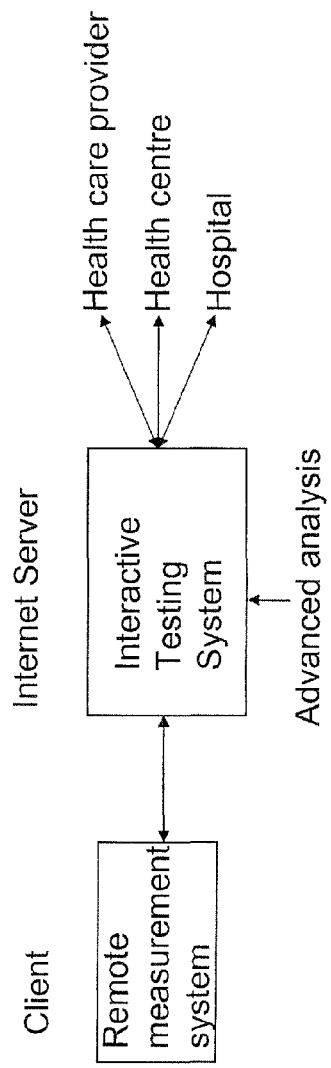
FIG. 1 schematically shows the structure of the service provided by the system according to the invention.

There are three types of 'clients' that are expected to use this service. First type is individual persons, who want to subscribe to the service of carrying out the measurements themselves and to receive health profiles from the interactive testing system. Some of these persons will also subscribe to a service, where a health care provider receives the health profile from the interactive testing system and evaluates it. The second type is family doctors, health centres, medical laboratories, hospitals and other institutions that provide health care service of people. The third type is schools, households, companies, sports clubs and similar ones that want health check for their members based on specific measurement instruments. The structure of the service is illustrated by the FIG. 1.

The client can choose a health care provider, family doctor, health centre, hospital, coach of a sport or some other instance. If the client chooses that the health profile is to be sent further, that instance is informed of that it may receive health profile from this client and possible some analysis. Furthermore, the instance will receive instructions of how to use the services of the interactive testing system, for instance, how historical data for the client can be viewed, how special statistical analysis can be carried out, how to obtain decision support for diagnostic purposes, how to add laboratory data to the client's data and similar instructions such that the services can be utilised effectively.

The measurement instrument is connected to the interactive testing system centre through a network, such as the Internet. The interactive testing system offers different services, when an instrument has been registered. The services are of the type:
1. When an instrument has been registered, it can be used to measure the chemical content of the biological tissue, such as liquids blood, urine and saliva. This can be carried out for any person, who has been registered at the interactive testing system. When the measurement values of the instrument have been sent to the interactive testing system, the client will receive information of how the person is located relative to a normal population.
2. The client can ask for monitoring of a special value of some health related parameter in the blood or urine.
3. The measurements of the client can be forwarded to a health care provider. The health care provider may also receive extensive statistical analysis of the data. On the basis of this the health care provider may reply to the interactive testing system. The interactive testing system forwards it to the client and will store the communication.
4. The client can be a patient that has been discharged from a hospital. The service can be used as a remote supervision of the patients. At regular time intervals the patient carries out the measurements, which are sent to the hospital. The hospital replies in an email, how the situation is progressing.
5. The health care provider can provide with supplementary measurements to the interactive testing system.
6. The interactive testing system can be used for decision support to the health care provider.

The purpose of the services is to provide with Health Profiles of the persons that communicate with the interactive testing system. Thus the results of the analysis are how the measurements are situated compared to a population that is appropriate to compare with. The service is provided to everybody that has an instrument registered at the interactive testing system.

Remote Measurement System and Remote Measurement Instrument

The interactive testing system comprises one or more remote measurement systems. The remote measurement system generates measurement data from the measurement of the biological sample. The remote measurement system furthermore communicates either directly or indirectly with the central server through a network, preferably the Internet. In the remote measurement system a display unit is available for displaying the health profile when received from the central server.

The remote measurement system may comprise both a measurement instrument and the means for forwarding measurement data, i.e. a communication unit integrated in the system, or the measurement instrument may be separate from the communication unit. In the latter case the communication unit may be a conventional computer and the measurement instrument may be adapted to connect to the computer, for example through a USB port. The means for forwarding measurement data may be any conventional communication unit, such as a communication unit in a conventional personal computer for communication on the Internet. Every measurement system has a well-defined communication address (for example an IP-address) and are communicating with the interactive testing system centre through this address. All communication between the central server and measurement system is preferably encrypted for secure communication.

Measurements can be carried out at any time and by anyone, who has been authorised to use the measurement instrument according to the invention. More than one person can use the instrument for measurement purposes. The measurements are carried out on biological samples, preferably body fluids, such as blood, saliva and urine.

In either case the measurement instrument is one, which has been clinically tested to give sufficiently precise measurements of the body samples, such as blood, saliva and urine. Through these clinical studies there have been established a reference data base, which assists in the statistical analysis of measurement data. There are many instruments that can be used, which give sufficient precision. An example is appropriately calibrated instruments based on optics, such as NIR, IR and FT-IR instruments, which can be produced cheaply for home usage.

It is preferred that a measurement instrument according to the invention gives information on molecular level of the chemical components of blood, urine and saliva, and forwards the raw measurement data to the central server for analysis to generate measurement values. An instrument may be based on a Near Infra-Red technology, and the data received may be interferograms or spectra based on Fourier Transform. For instance it may give 3200 data values for one sample, which has been measured. All data values are sent to the server. In this case $3 \times 3200 = 9600$ numerical values may be sent to the central server, if a sample of blood, urine and saliva has been measured. At the server the estimate of the chemical components are carried out, preferably using chemometric methods to estimate the chemical components, thereby obtaining measurement values. Furthermore, analysis of patterns or fingerprints gives rise to measurement profiles.

The measurement instrument preferably can detect changes in the blood, saliva and urine, which the person cannot feel or detect. If the person carries out the measurements at regular time intervals, it is possible to detect changes that may lead to diseases. The diseases: "Rheumatism, Cardiovascular diseases, Metabolic disorder, Diabetes 2, Glandular diseases, Infection diseases, Lung diseases and Cancer diseases" all start by changes in some chemical components in the blood, which can be detected at an early stage. Thus the service can be used to provide with an early warning within each of these types of diseases.

The chemical components in the morning are for a normal person relatively constant. The caffeine from the coffee drinking the previous day has disappeared from the blood. Similarly, at normal alcohol consumption the alcohol in the blood has disappeared from the blood. Adrenaline due to tense situation previous day has disappeared. Thus, if a person is measured in the morning, the results of the chemical components in blood, saliva and urine will be relatively constant.

If a person is measured early morning once a week over 10 weeks, it will be possible to define the 'fingerprint' of chemical components, which is natural for the person. Furthermore, such "fingerprint" of chemical components is normally individual, so that each individual "fingerprint" differs from fingerprints from other individuals. It is recommended to carry out each measurement twice over these 10 weeks period in order to detect the variation in data values due to the measurement situation. Thus, after a 10-week period it is possible to determine the levels of the chemical components, which are natural for the person, and the type of variation that may be expected from day to day.

In a preferred embodiment the person, who has acquired a measurement instrument according to the invention, and carried out the 10 weeks measurement plan, has established a safety line to the central server. The safety line can be used as a service to supervise ones own health care, or to improve ones health conditions. Persons needing special diets can use the service to find an appropriate diet, which fits them well. A sports person can use it to supervise the parameters related to the performance within the sports field. It can be used to document that the person is not using doping means to achieve performance, although the service does normally not give an official certificate of that the person has not used doping means.

Health Profile.

The basic service is an on-line service. Based on the analysis of the measurement data as well as the measurement values generated at the central server, the client receives a health profile. If a health care provider has been connected in respect of the client the health care provider also receives the results of a standard statistical analysis. A health care provider may require a special health profile for a client. For example a person, who has been diagnosed as belonging to a Diabetes 2 risk group, may receive a special health profile that assists the client in supervising his/hers health.

The criteria that are used in designing this service are preferably 'direct, simple and robust'. By 'direct' it means that the analysis leads to information of whether the situation is normal or not. That all of the standard analyses are simple and robust means that they can be carried out for all, and the results are easily communicated to a health care provider. A more detailed analysis can be asked for by the client or the health care provider. The health care provider can use the services of central server to identify the analysis that he/she wants to be carried out.

At the central server an analysis of the incoming measurement data of the biological sample is carried out. The chemical components of the sample are computed to generate measurement values and/or profiles and a health profile is generated based on the measurement values. The remote measurement system receives the health profile, which in a preferred embodiment shows how the basic health parameters of the person are located relatively to a normal population of corresponding age, sex etc. The health profile may be presented as a table of data values showing the present measurement values of the parameters and optionally a graph showing the last 10 measurement values of the parameters. The graph may show the historical developments of the measurement values. The health profile may for example include information of for instance, cholesterol, blood percentage, total protein, sodium, potassium, fat content, sugar level in blood, urine and saliva, depending on what was measured.

Furthermore, at the central server, further analysis of the raw measurement data may be performed. This includes processing of the raw measurement data into fingerprints or patterns for comparison with references for one or more diseases.

Based on the measurement values as well as on the result of analysis of the profiles, the health profile may contain further information. In one embodiment the remote measurement system may receive one of several types of comments to the analysis that has been carried out. It may be pointed out that no special features have been found. Secondly, that some special features have been found and it is recommended to carry out more frequent measurements than what has been done previously in order to be able to carry out necessary or appropriate analysis. The third type of comments is that some significant features have been found, and it is recommended to contact a health practitioner. A fourth type of comments is that transmission of a recommendation of following the advice of a health care provider. Such advice may either be generated based on the actual health profile or have been generated before and just reiterated.

In a preferred embodiment, when a client has carried out a measurement, and all measurement values from the instrument are sent to the central server, the client will preferably within a minute or so receive the health profile.

Preferably the health profile contains the following information:
1. A data table showing the values of some chemical components in the blood sample, and how these values are related to a normal population.
2. A graph showing the historical values of these parameters (optional up to last 30 measurements)
3. Comments on the results of analysis. The results are presented either that nothing was found or recommendation to contact the health care provider.

In general, as stated above, the client will preferably receive an answer within a minute or so of the basic health parameters after the data have been sent to the central server. But at the server extensive statistical analysis may be carried out on the new measurement data and the available historical data. In a preferred embodiment intensive analysis is carried out for each of the eight areas:
  Rheumatism
  Cardiovascular diseases
  Metabolic disorder
  Diabetes 2
  Glandular diseases
  Infection diseases
  Lung diseases
  Cancer diseases If some special features are found, the client may later receive a new message, which recommends contacting the health care provider.

Health profiles may be different depending on what has been asked for. When people subscribe on the service, they may ask for a general analysis of the blood and urine. In this case the basic parameters of blood and urine are communicated back to the client. Furthermore, the client receives a short review of the historical values or values over some appropriate time periods. If a trend has been detected, forecasts for the next three periods are presented as a standard. Limits that are normal for the population are presented. The limits are to be understood that 99% of the population, which the client is compared to, may be expected to be within these limits.

Furthermore, if a health care provider is connected to the central server, the system may further include means for allowing the health care provider to provide recommendations to be included in the health profile forwarded to the remote system.

Central Server

The central server processes the raw measurement data provided by the remote measurement system as well as generates measurement values from the processed measurement data. Furthermore, the central server comprises means for storing the measurement values, in a preferred embodiment both storing actual and historical values as well as normal population ranges for references. In a preferred embodiment there are two databases at the central server. The first one has been developed by clinical study using the given measurement instrument according to the invention. It contains reference values for the each of the diseases, which has been clinically studied in relation to the measurement instrument. The other database contains measurement values that have been carried out remotely and received by the server.

Preferably, as a standard three types of analysis are carried out. The first is an analysis aiming at detecting if there is a trend in data. If there is a trend in some of the parameters, forecasts are made and the results are evaluated in the light of the forecasts. The second type of analysis has the purpose to find out if there have occurred significant changes in the basic parameters over recent period. The purpose of this analysis is to find out if parameters are normal, or if there is developing a pattern that may influence on the health of the client. The third type of analysis if there are patterns in data that point to risks in one or more of the types of diseases in focus at the interactive testing system. The results of this analysis are reported back to the client in a way that the client is recommended to see a doctor, if significant risks have been found. A health care provider may further receive the results of analysis and explanation of the patterns found. However, preferably no specific diagnoses are reported to the remote user.

Preferably an expert knowledge system is used to evaluate the incoming measurement data. There are two types of evaluations carried out. One type is using chemometric methods to evaluate how new measurements are located geometrically in the light of the clinical database. The other type is the use of Neural Nets to identify if the present values match the measurement profiles, which have been developed, using Neural Nets, from the clinical database. Risk evaluation is based on both types of methods. If both agree that there is significant risk of a disease, an early warning is issued. There is preferably an expert knowledge system for each illness, which is considered from the eight types of diseases.

The statistical analysis consists of two parts:
a) Specially developed chemometric methods are used to identify chemical components in the biological sample, such as blood, urine and saliva. Furthermore, the developed methods are used try to identify special 'profiles' in data, which the clinical studies have suggested may be relevant for detecting early stages of the diseases. The results of this part of analysis are sizes of chemical components in blood, urine and saliva, which may be of importance for the diseases in question, and study of these in relation to the clinically tested data.
b) Each type of disease has a specially developed pattern recognition method based on Neural Nets. These pattern recognition methods are developed on the basis of the clinical data and with the assistance of clinical experts. The resulting expert knowledge system reflects the knowledge and procedures of the medical experts. When a client is studied, the knowledge system receives input from the chemometric methods. At first a client has zero chances of belonging to the risk group of this disease. When more and more measurements arrive the odds for this disease may increase. When significant risk has been detected, the client may be asked to carry out measurements at some specific time intervals, e.g. weekly. In this case also the health care provider is informed of the results found.

These two types of analysis are carried out for diseases considered here. For instance, different types of cancer are studied. As an example, evidence against colon cancer is studied. In the clinical database there are detailed measurements of a number of patients that have been diagnosed by colon cancer. The chemometric methods analyse chemical components and special measurement 'profiles' in data (e.g. increased production of proteins in the blood and increased amount of proteins in the urine), which are frequent for colon cancer. The specific expert knowledge system used here has been developed with the assistance of medical experts in the field. Evidence is accumulated for each client until a possible significant result is found, in which case the health care provider is informed and results presented. The information provided is given in the terms that the medical experts specified for giving evidence of colon cancer.

For each client possibilities of different types of illnesses within each of these eight groups of diseases are studied. One collection of chemometric methods are used for each type of illness. Furthermore, one set of expert knowledge system is used for each. The type of chemometric analysis and knowledge system differs from illness to illness. Each set of tools have been developed to provide the medical expert of the illness with appropriate information for decision support.

Furthermore, the central server comprises means for communicating with the one or more remote measurement systems in order to forward measurement values and health profiles to the client.

Communication with Health Care Providers and Others

The basic interactive testing system includes the remote user, i.e. the client, and the central server, and communication is conducted between these two entities. However, it will often be relevant to include other entities in the communication flow in order to optimise the prevention and/or monitoring of diseases.

First of all, the interactive testing system may provide means for enabling a health care provider to communicate with the central server. In the most basic form, an assigned health care provider receives the health profile generated for the remote user according to some agreements, which have been signed and confirmed. The agreement may be that the health care provider receives a report each time measurements are carried out, at some specific time intervals, only if significant results have been found or according to some other contract. The interactive testing system will not provide with a direct diagnosis. But if a person has been measuring himself/herself over a period of time, the advanced methods of pattern recognition at the interactive testing system will detect an early stage of a disease. The health care provider will get the results of the analysis, and will be able to use it as a decision support.

Additionally, it may be preferred if the health care provider can upload laboratory measurements for the client, for these new sets of data to be included in the statistical analysis. The health care provider can require a medical report with and without the new laboratory data.

Furthermore, the health care provider may, in addition to or instead of the health profile, receive or request to receive an expert report based on analysis of the measurement values and/or measurement profiles. For example a clinical database in the central server may suggest that some chemical components in blood, urine and saliva should be estimated and analysed. The expert knowledge systems may then suggest possible evidence of the illnesses that are being detected and communicate the results in medical terms. For example, if one of the expert knowledge systems has detected a significant risk of an illness, a report is prepared, which expresses in medical terms the results found. The report will reflect the procedures, which the clinical doctor would use in the evaluation of the present measurement values and the report could be used as a support for the decision of the clinical doctor. The report can, besides medical information, contain recommendation concerning lifestyle. The report may be forwarded to instances that have been agreed upon.

Other entities authorised to receive reports from the central server may be patient unions. There may be an agreement of that a patient union will receive a report, if significant development has been detected. For instance, there may be an agreement that the union of diabetes patients may receive the report, if there has been detected a significant risk of diabetes 2. Such a report may be identical to the health care report forwarded to the remote user, or more specific or more general.

In a preferred embodiment the person responsible for the measurement instrument according to the invention owns the data that have been sent by the measurement instrument. The person can at any time logon the server and delete part or all of the data that have been received from the instrument. Furthermore, the owner of a measurement instrument according to the invention can at any time log-on the server and view the historical development of some health parameters. The health parameters viewed can be different from the ones that are received, when measurements are carried out.

If authorised, other entities, in particular a health care provider, may be able to logon the server and view the historical development of some health parameters.

Remote User

The remote user, or client, is normally the individual to be tested. However, there can be an agreement that for instance a hospital can send measurement data from a measurement instrument according to the invention to the server with the purpose of analysing the data. The hospital/health practitioner will receive the results of analysis. The data may be values from a measurement instrument according to the invention supplemented by laboratory measurements. The numerical values that have been analysed may or may not be stored in the database at the server.

The remote user can subscribe on the service that the interactive testing system provides with in two ways. The subscription can concern receiving health profile only, or it may also include a health care provider.

I. A client registers for health profile. The client can buy or rent a measurement instrument, which for example can measure the chemical content of blood, urine and saliva. When the client has carried out the measurement, the data are automatically sent to the interactive testing system, and the client receives back a health profile as described above. The measurements are stored in a database at the central server, and the client can at any time carry out these measurement, retrieve measured values and the historical development of the health parameters. The client may allow for allocation of other entities to communicate with the central server relating to his or her data.

II. A client registers for a communication service with a health care provider. A client can register for communication with a health care provider (family doctor, health centre, hospital etc). At this registration the client specifies the degree of service, which the health care provider is giving. When a client is registered for this service, the measurement values and/or measurement profiles are forwarded to the health provider. The health care provider answers back to the interactive testing system, which sends it back to the client. This communication is stored at the interactive testing system for later reference. The client can agree with the health care provider that further data and information can be stored at the interactive testing system.

When a health care provider is involved in the service, he/she can utilise the different services that are made available at the interactive testing system, like advanced statistical analysis, decision support, on-line services etc.

Figure 2:
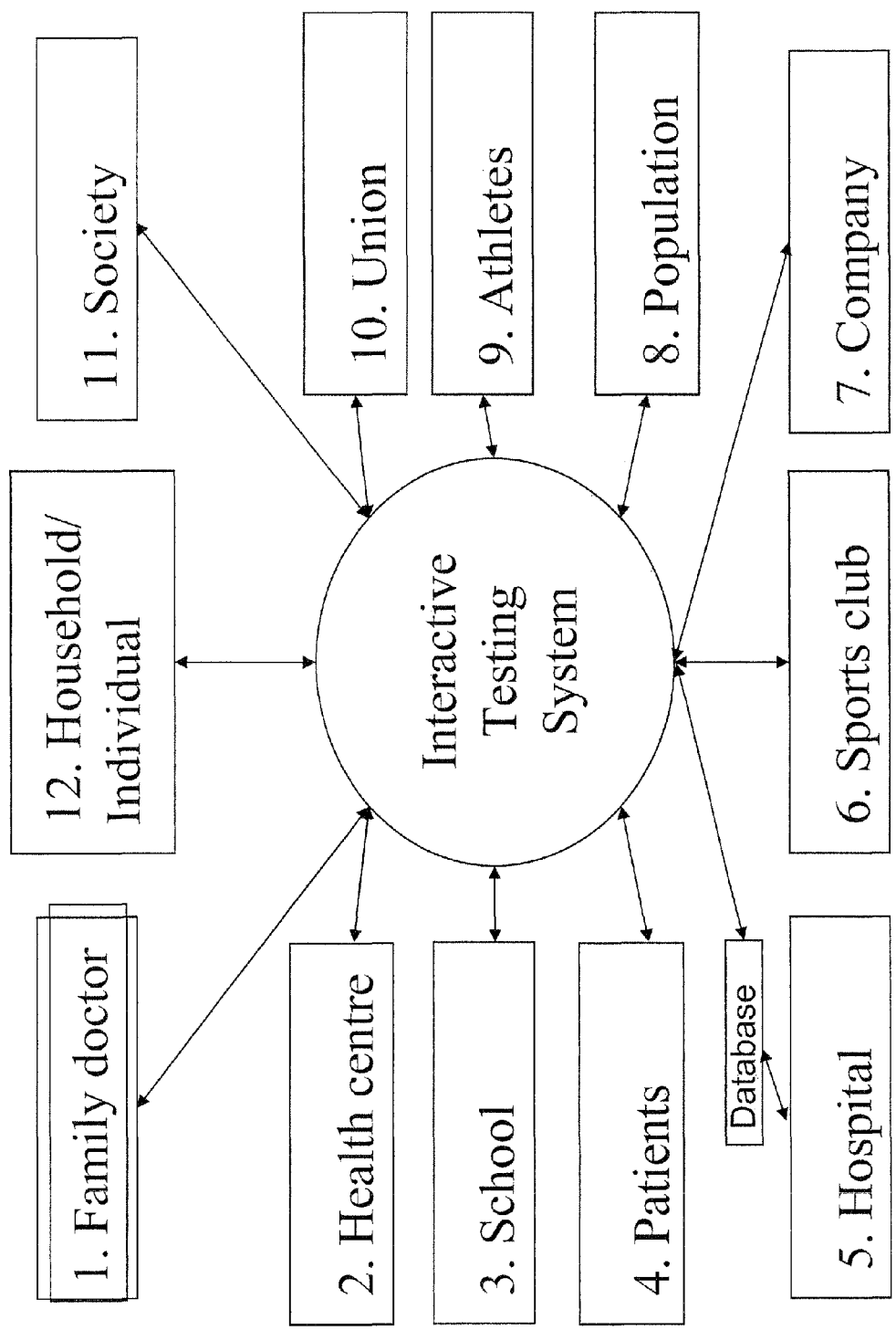
FIG. 2 schematically shows an overall view of the type of services delivered by the present invention.

FIG. 2 gives an overall view on the type of services delivered by the present invention.

A review of the services is as follows:
1. Family doctor. A family doctor has an approved instrument to measure e.g., blood, urine and saliva. The measurements can be checked against the data base at the interactive testing system and provide with health profile for the person. The doctor can utilize the services offered at the interactive testing system in different ways to improve the health care task.
2. Health centre. At a health centre there are certain instruments that can measure beside the chemical contents of blood, urine and saliva, also e.g., heart function and blood pressure. The data can be sent to the interactive testing system for investigation.
3. School. A school has an instrument to measure blood and urine. The data can be checked at the interactive testing system and return a health profile for each pupil at the school.
4. Patients. A patient sends regularly their data that they have measured themselves. The interactive testing system centre carries out the monitoring and supervision of their health status, and sends the results to the doctor/hospital in question. The answer from the doctor/hospital is sent back to the patient.
5. Hospital. A hospital establishes a database of health data that is supervised and updated by the interactive testing system. The hospital uses the database for its own analysis of health and diagnosis that is associated with these measurements. This means that the database is stored at the hospital instead of at the interactive testing system. The interactive testing system only carries out the analysis.
6. Sports club. A sports club, like e.g. a golf club, provides with a service to their members that they can be measured and data analysed at the interactive testing system. There may or may not be a doctor that receives the results of the measurements.
7. Company. A company can provide with a standard analysis of the health of the staff. The health questions that the company can subscribe on can be a) recent use of drugs, b) extensive use of alcohol, c) general health condition, and others.

8. Population. A population can be checked for special symptoms like e.g., diabetic 2.
9. Athletes. Athletes can subscribe on the service that they deliver samples of blood and urine and they receive health profiles that show that they are clean with respect to a given collection of drugs. This is not a certificate of not using drugs, but over time documents no usage of drugs.
10. Union. A union of people, like e.g., labour union, private clubs or associations, can provide a service to its members that they can obtain at regular time intervals a check of their health by the service of the interactive testing system.
11. Society. The people of a society like e.g., a village with access to Internet can be offered the service that they can be supervised by the interactive testing system using the measurement instrument in the village.
12. Household/Individual. A household or an individual can choose to invest in a simple measurement instrument that can be connected to the interactive testing system through Internet, and subscribe on a health profile service from the interactive testing system.

Furthermore, the interactive testing system according to the invention may be used for monitoring individuals suffering from a diagnosed disease as well as for supervision of patients, elderly and/or handicapped persons.

The hospitals are often being filled by patients that have finished treatment and are only at hospital for monitoring purposes. These patients would be able to be sent home, if they could be supervised remotely by a nurse or a doctor. E.g., if a patient has been treated for cardiovascular disease, the patient could measure himself/herself and fill out a blanket, which is required by the hospital. The responsible nurse or doctor could use the analysis carried out at the interactive testing system as a decision support for further analysis.

Elderly people could be longer at home. If they carry out regular measurements, e.g., once a month, the family doctor could follow up on the measurement analysis, and decide if further analysis is needed in the light of the analysis from the interactive testing system. In this way people can come to proper treatment much earlier than if the disease have already occurred and then start the medical analysis.

Handicapped people or people that have been diagnosed as belonging to a risk group of one of the above diseases can stay at their homes. By regularly measuring the person it is possible to supervise the persons and detect, when direct efforts are needed.

Example of Steps in the Interactive Testing System Service

The different steps or aspects of the interactive testing system service are presented as follows:

Purchase of a Measurement Instrument According to the Invention

1. A customer buys or rents a measurement instrument (typically small sized, such as 15×15×10 cm). At the time of purchase there may be assigned a health care provider, who will receive information from analysis. Assignment of a health care provider can be done at any time. Different users of the instrument can have assigned different health care provider.
2. The customer receives a PIN code, for example by mail.
3. The customer carries out the necessary installation of software to secure connection to the central server.
4. When the instrument is used the identification is the PIN code and a personal identification. The identification is the one provided by the customer. At later measurements the person is identified by the PIN code and name.
5. The customer carries out the measurements of blood and/or urine and/or saliva. The instrument (possibly through the computer) sends the measurement data to the central server. Within a minute or so the customer will receive a data sheet, a graph and some short remarks concerning the findings. The data sheet will show how the person is in proportion to a normal population.

Usage of a Measurement Instrument According to the Invention

1. At first the person is identified. PIN code and name is given. It is also informed if this is the first time that the person carries out the measurements. This is important because later measurements are rejected, if it is detected that they do not come from the person specified.
2. The measurement of a sample of blood and/or urine and/or saliva is carried out. The measurement values of the instrument are sent to the central server. Within a minute or so the person will receive the health report, for example in the form of a Data Sheet and a Graph.
3. The person can select that some special information should be sent back. Diseases in focus may be: Rheumatism, Cardiovascular diseases, metabolic disorder, Diabetes 2, Glandular diseases, Infection diseases, Lung diseases and Cancer diseases. In agreement with the health care provider the person can, instead of the standard data sheet, receive information relevant to these diseases.
4. The person will receive a message, which gives an overall answer of the results of analysis that have been carried out. If special features have been found, there may be recommendation to contact the health care provider.
5. If there is assigned a health care provider to the person, the results of analysis can be sent to further to the health care provider. This health care provider will receive a report on the results of the analysis. There will be the option that also the historical development is sent further to the health care provider.

Customer's Use of the Data Centre

There are two types of services that are provided, Data Service and Administrative Service. The person identifies him- or herself by a user name and password.

Data Service

1. The person fills out a form that specifies which data are wanted to look at. The person specifies data, period and the way the results are required to be displayed.
2. The historical data are shown in the desired way. The person can select different ways to present the data.
3. The person can choose that specific data are sent further to the health care provider, who is assigned to the person.

Administrative Service

1. Concerning payment of the service
2. Assign a health care provider to a person.
3. Delete or remove data from the database of the central server.
4. Problems with the interactive testing system service
5. FAQ's Health Care Provider Receive Measurement Data 1. Receive present measurements and the historical development for a person.
2. Receive the results of the analysis of data. It is aimed at that the report can be used as a decision support for the health care provider.

Use of the Central Server
1. After filling out username and password, a form is presented. This is used to select data from the database for the person in question.
2. It is possible to view historical data in different ways.
3. It is possible view recent decision support that has been suggested in the past.

Upload Laboratory Data to the Server
1. The health care provider can choose to upload laboratory data that are available for a person. The type of files follows hospital standards for laboratory files.
2. The health care provider can ask for extended analysis based on the measurements and uploaded data. New extended decision support is made available in the light of the new data.

EXAMPLES OF APPLICATIONS OF THE SYSTEM AND METHOD ACCORDING TO THE INVENTION

Service 1: Comparisons to Normal Population

The user of the interactive testing system service registers on an appropriate form. The information from the form is included in the registry of clients to the interactive testing system service. When measurements are carried out, the client specifies the user name and pin-code. This identifies the client. The measurement values are received by the interactive testing system and analysed further. The analysis is partly based on the present values, historical values and a large reference database. The client will receive information on the values of basic health parameters (e.g., cholesterol, blood percentage, sugar level, fat etc) and how these values are located relative to a normal population. If a detailed statistical study indicates risks of the client's health, the person will be recommended to see a doctor. The risk groups analysed are some types of cancer, diabetes 2, some common cardiovascular diseases, internal infections, stress indicators and similar indicators that indicate risks for the health.

Execution Example 1

A typical example of the service is as follows:
A client fills out a blanket asking for user name and pin-code. The user can also fill out information on weight, sex and age. Measurement of blood and/or urine and/or saliva is carried out.
The client receives back information on the basic health parameters and how they are located relative to normal population.
If special risks have been detected at the interactive testing system, the client is informed of recommendation to seek a doctor. Otherwise the client is informed of the no special features have been found.

Service 2: Monitoring Special Levels of Values

A client can ask for monitoring of special parameters in blood or urine. This can be important for persons that have been diagnosed in some risk group. E.g., persons that are in the risk group of diabetes 2 or have been diagnosed with diabetes 2 can carry out regular measurements and be informed of the parameters that are relevant for these groups.

Execution Example 2

A typical example of the service is as follows:
A person that is severely overweight can ask for monitoring the fat level in the blood.
If some results have been found that are judged special, they are marked with a comment. In this case there may be recommendation to contact a doctor.

Service 3: Communication with a Health Care Provider

The interactive testing system can arrange communication to a health care provider. When such a communication contact has been established, the results of measurements and associated statistical analysis are sent to the health care provider, who typically would be the family doctor. He/she receives the email from the interactive testing system and answers the email, which is stored at the interactive testing system and forwarded to the client. The health care provider can, like the client, at any time logon the interactive testing system site and study historical data of the client.

Execution Example 3

A typical example of the service is as follows:
The client carries out measurements that are sent to the interactive testing system. The client receives the standard health profile that was asked for. The measurement values and the results of analysis are sent to the health care provider. The health care provider answers the email. It is stored at the interactive testing system and sent further to the client.
This communication is stored at the interactive testing system and can be viewed at any time by the client and the health care provider.

Service 4: Supervision of Patients

It happens often that patients are kept at the hospital after treatment, although the treatment has been completed. This is often done as a safety measure. But the present service can be used to release the patients earlier than normal and instead use this service to supervise the patients. The patients will be able to measure themselves or by a visiting nurse. The results of measurements, together with a blanket filled out by the patient or the nurse, can be sent to the interactive testing system, which analyse the results further and sends the results to the hospital. The doctors at the hospital can evaluate the results and send the evaluation back to the patient. This can be carried out while the visiting nurse is at the patient. If the hospital is ready to answer, the technology can complete the tasks in few minutes at most.

Execution Example 4

A typical example of the service is as follows:
The patient at his home, or a nurse, carries out the measurements. A blanket concerning the body temperature and other actual information is filled out. The measurements and the blanket are sent to the interactive testing system that analyse the data. The measurements, the blanket and the results of analysis are sent to the hospital. The hospital answers with a new email to the interactive testing system, which is sent further to the patient and also stored at the interactive testing system.
The interactive testing system stores the communication between the patient and the hospital. This information can be retrieved by the hospital or a health care provider that is authorised to look at the patient data.

Service 5: Supplementary Laboratory Measurements

A health care provider can in agreement with the client decide to store supplementary laboratory measurements at the interactive testing system. These new measurements can enter the statistical analysis that the interactive testing system carries out and thus provide with more detailed results for the client in question. The client can view these new data, and the health care provider can study the historical development of all data, both the ones that the client measures and the ones that the health care provider supplies.

Execution Example 5

A typical example of the service is as follows:

The interactive testing system receives the new measurements from a client. The results are sent to the health care provider, who suggests that the person should go through some laboratory tests. When the health care provider receives the laboratory measurements, they are sent to the interactive testing system for storage and integration into the interactive testing system service.

The client can view the results of the new laboratory measurements in the light of the personal data and their development over time. The health care provider can ask for diagrams over time of a health profile required analysis.

Service 6: The Use of the Interactive Testing System for Decision Support

The interactive testing system provides with a database, where health care providers can store different background information. The information stored is what the health care provider considers relevant for the client in question. The interactive testing system provides with advanced pattern recognition methods that can assist the health care provider in making correct decision for the person in question. The health care provider may propose different alternative types of diseases for the person. The methods will assign probabilities to each of the proposed diseases. This allows a check for numerous diseases, detection of trends or symptoms for unbalances that might result in diseases.

Execution Example 6

A typical example of the service is as follows:

A health care provider has a lot of background information on a client. The health care provider may want some of this information to be included in the database of the interactive testing system for decision support. The health care provider logs in the interactive testing system's decision support database. Blankets shown are filled out. Furthermore, diseases are specified, which are to be analysed. When blankets have been filled out the health care provider receives probabilities showing the rating for the different alternatives that have been specified.

The health care provider can provide with further information and ask for new analysis. The health care provider can ask for that the analysis is carried out at regular time intervals, and if a probability exceeds some limit, an email should be sent to inform of the change in the clients health.

Figure 3:
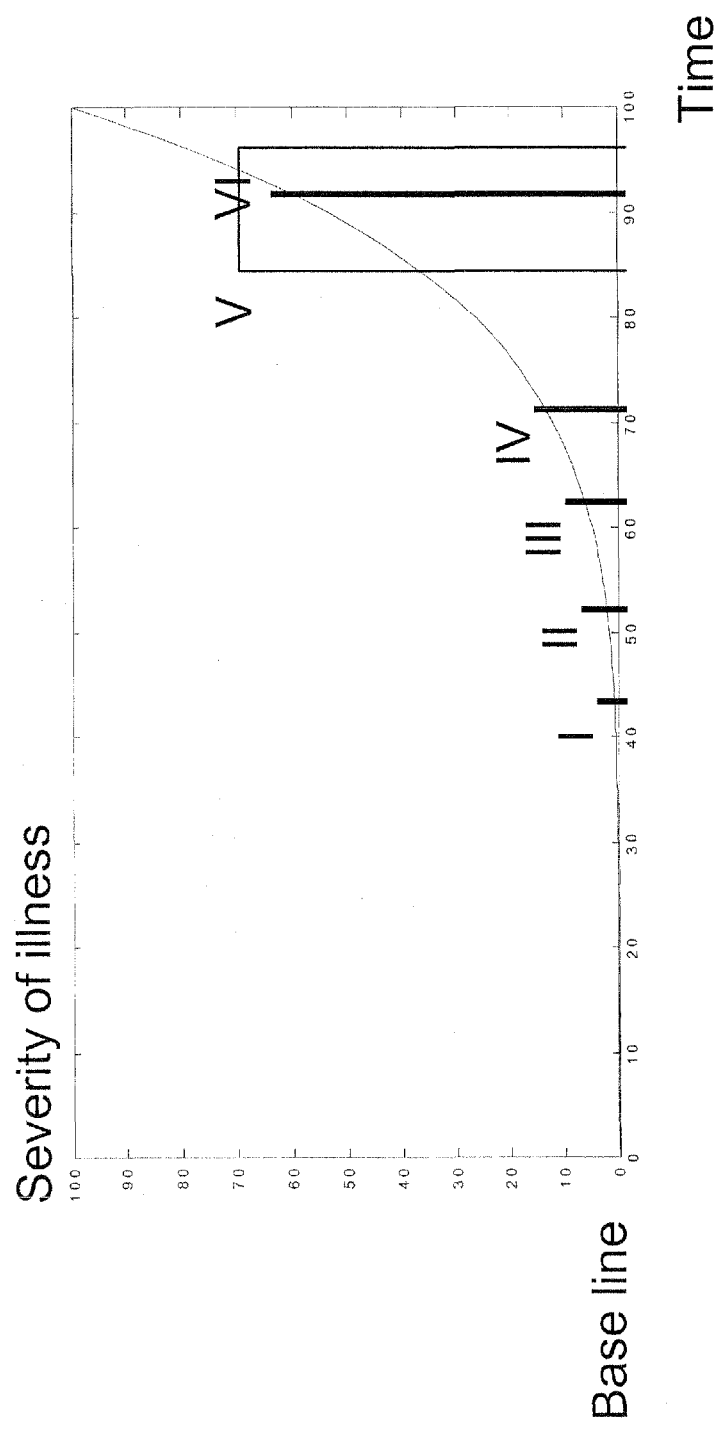

The curve in the FIG. 3 shows typical development of the severity of a disease considered in this invention. The base line indicates the normal situation for a person. Then there are typically following stages in the development of the disease.

I Molecular changes in the blood due to the illness can be detected.

II Pre-clinical stage. The changes in the blood can be measured by a measurement instrument according to the invention.

III The person can feel that something may be wrong. It can be feeling tired in the morning, headache, stomach pain or feeling of some discomfort. The feeling may disappear by headache pill or coffee.

IV The medical health practitioner can see or feel that something might be wrong. If the symptoms can be identified, the patient may be sent to a hospital/specialist for further treatment. It may be that the medical health practitioner only prescribes a headache medicine or something similar.

V A hospital treatment starts. It may vary over some time.

VI An irreversible stage. The illness is not curable, when it is beyond this level.

Illnesses within the following types of diseases are considered: Rheumatism, Cardiovascular diseases, Metabolic disorder, Diabetes 2, Glandular diseases, Infection diseases, Lung diseases and Cancer diseases Discussion of FIGS. 4-8

Figure 4:
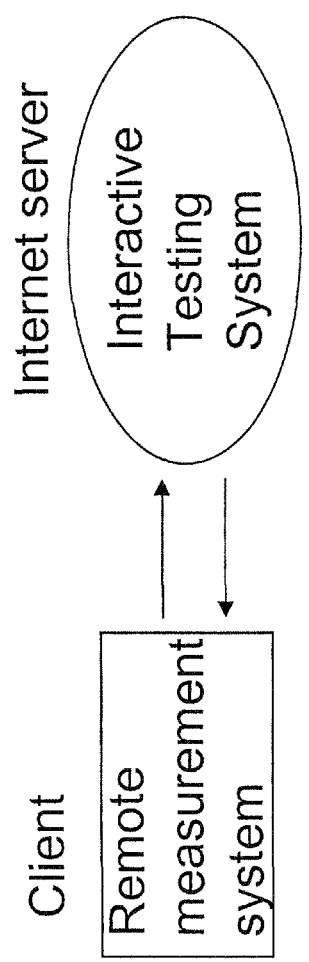
FIG. 4 shows a situation, where there is not connection to the health care system.

FIG. 4 No Connection to a Health Care Provider

A client carries out measurement using a measurement instrument according to the invention. The client receives back values of the parameters that have been asked for.

EXAMPLES

A sports person measures the blood and asks for the value of haemoglobin value. He or she may only be interested in the amount of the red blood corpuscles.

A pregnant lady measures blood once a week and only asks for the value of the blood percentage.

A person only measures urine once a month. He or she is only interested in the amount of sugar in the urine.

A person measures saliva once a month. It is used as guidance if further measurements should be carried out.

Figure 5:
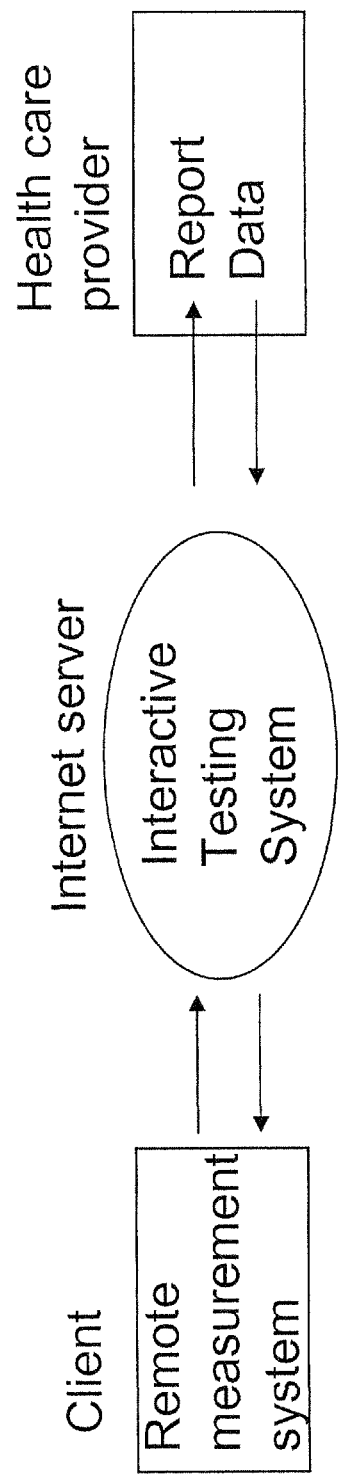
FIG. 5 shows the normal situation, where there is a connection to a health care provider.

FIG. 5. A Normal Situation with a Connection to a Health Care Provider

A client, a person, carries out measurements that are sent through Internet to the server. The measurements are analysed. A health profile is returned to the client. A Report is sent to the health care provider. The health care provider may have further data, which can be uploaded and included in the analysis of the Interactive Testing System.

EXAMPLES

A person buys or rents a measurement instrument according to the invention.

There is an agreement that the family doctor will receive a report from the Interactive Testing System twice a year.

A person has been diagnosed with diabetes 2. There is an agreement that the person measures blood and urine once a month. The person will receive values of some selected parameters and the family doctor receives the health report from the Interactive Testing System.

A family doctor finds the health of one of his patients not be quite in order. The person is asked to measure him- or herself once a month and the health report sent to the doctor.

Figure 6:
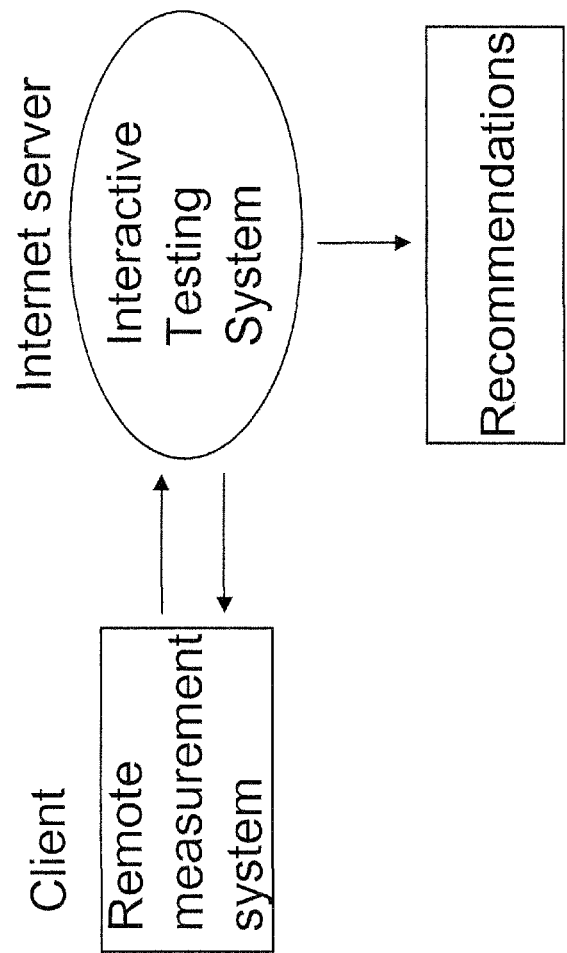
FIG. 6 shows the situation where a company uses the service to supervise the health of staff members. Similar situation is at school in supervising the health of children, old peoples' homes, ship crew, sports club etc. Recommendations are provided.

FIG. 6. Supervision of Health of People

The service is used to provide with recommendation on the persons measured.

EXAMPLES

A company hires a nurse to come twice a year to measure each staff member. If special features are found, the company only wants to know what is best for the person. If for instance, the person has been stressed over longer period of time, and some effects are detected, the company wants instructions and recommendations for the person. If it may be serious, the person may be asked to contact a health practitioner. The service may be mainly used to improve the lifestyle of the staff members.

Similarly, supervising the health of children at school, old peoples' home, ship crew, sports club members etc the main issue may be if the health is normal or not. If not the person may be advised to seek a health practitioner. But for instance a sports club may not be interested in a connection to a health care provider.

Figure 7:
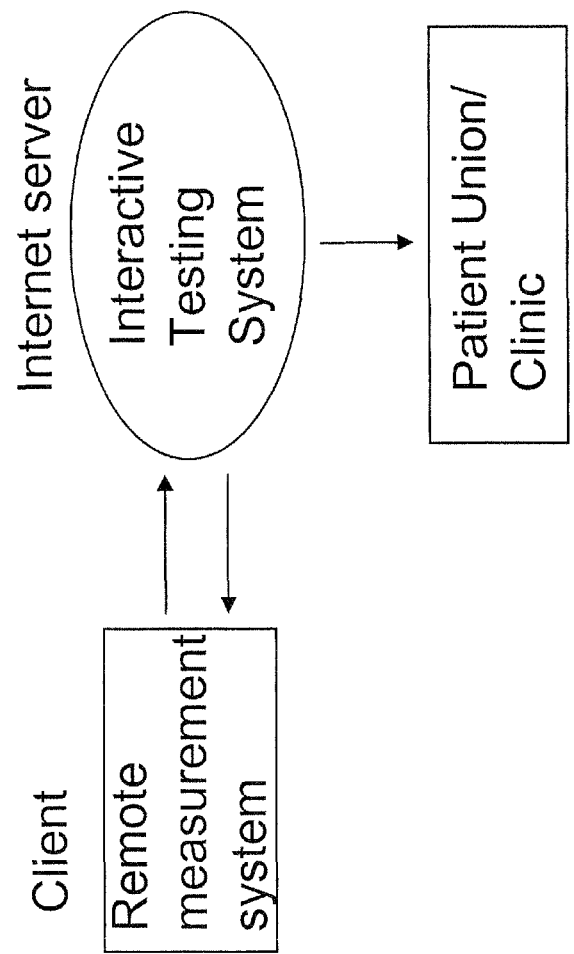
FIG. 7 shows the situation, where only significant risk is forwarded further. Otherwise there is not a connection to a health care provider.

FIG. 7. Only Significant Risks are Forwarded

It may be required only to forward a report, if there have been found significant results.

EXAMPLES

A union of diabetes patients wants a report, if a significant trend towards diabetes 2 has been detected.

A client arranges with a clinic for cardiovascular diseases that the clinic will receive the report from the Interactive Testing System, if there have been found some clear indications of some cardiovascular diseases.

The invention claimed is:

1. An interactive testing system for analysing biological samples, said system comprising:
   one or more remote measurement system(s), selected from the group consisting of: Near-Infrared Spectroscopy, Infrared Spectroscopy, or Fourier Transform Infrared Spectroscopy, for measuring a biological sample, obtained from a patient, said remote measurement system generating measurement data from the measurement of said biological sample, wherein said measurement data comprises spectral data;
   a central server;
   means for establishing communication between said remote measurement system and the central server over a network;
   said remote measurement system further including means for forwarding measurement data from the remote measurement system to the central server through the network, and a display unit;
   said central server being operative to:
     receive and process said measurement data forwarded from said remote measurement system, so as to generate a set of measurement values corresponding to the biological sample obtained from said patient;
     store historical sets of measurement values previously generated from measurement data previously forwarded from said remote measurement system with regard to said patient, and/or store data comprising ranges of measurement values for a normal population;
     statistically analyze said set of measurement values with regard to said stored historical sets of measurement values and/or said stored ranges of measurement values for a normal population, so as to generate an individualized health report for said patient; and
     forward said individualized health report to said measurement system.

2. The interactive testing system according to claim 1, wherein the health profile comprises an early warning for a disease.

3. The interactive testing system according to claim 1, wherein the remote measurement system comprises a measurement instrument, wherein said measurement instrument includes the means for forwarding the measurement data.

4. The interactive testing system according to claim 1, wherein the remote measurement system comprises one or more measurement instrument(s), each being connected to a computer, wherein said computer includes the means for forwarding the measurement data.

5. The interactive testing system according to claim 1, wherein the measurement data consists of spectral data.

6. The interactive testing system according to claim 1, further providing means for enabling communicating with a health care provider.

7. An interactive testing method for analysing biological samples, said method comprising
   establishing one or more remote measurement system(s) for measuring a biological sample obtained from a patient, said remote measurement system generating measurement data from the measurement of said biological sample,
   performing a measurement using said remote measurement system obtaining measurement data,
   forwarding the measurement data to a central server, said central server being operative to store historical sets of measurement values previously generated from measurement data previously forwarded from said remote measurement system with regard to said patient, and/or store data comprising ranges of measurement values for a normal population,
   in said central server, statistically analyzing said set of measurement values with regard to said stored historical sets of measurement values and/or said stored ranges of measurement values for a normal population, so as to generate an individualized health report for said patient, and
   forwarding said individualized health report from said central server to the remote system.

8. The interactive testing method according to claim 7, wherein the measurement data consists of spectral data.

* * * * *